(12) United States Patent
Reik et al.

(10) Patent No.: US 8,298,529 B2
(45) Date of Patent: Oct. 30, 2012

(54) COMPOSITIONS AND METHOD FOR EPIGENETIC MODIFICATION OF NUCLEIC ACID SEQUENCES IN VIVO

(75) Inventors: Wolf Reik, Cambridge (GB); Hugh Morgan, Cambridge (GB); Chun-Fung Chan, Hong Kong (HK)

(73) Assignee: CellCentric Limited (GB)

( * ) Notice: Subject to any disclaimer, the term of this patent is extended or adjusted under 35 U.S.C. 154(b) by 650 days.

(21) Appl. No.: 12/226,094

(22) PCT Filed: Apr. 10, 2007

(86) PCT No.: PCT/GB2007/001304
§ 371 (c)(1),
(2), (4) Date: Oct. 13, 2009

(87) PCT Pub. No.: WO2007/128982
PCT Pub. Date: Nov. 15, 2007

(65) Prior Publication Data
US 2011/0138491 A1    Jun. 9, 2011

Related U.S. Application Data

(60) Provisional application No. 60/790,273, filed on Apr. 7, 2006, provisional application No. 60/797,942, filed on May 5, 2006.

(30) Foreign Application Priority Data

Apr. 7, 2006 (GB) .................................. 0607063.5
Nov. 27, 2006 (GB) .................................. 0623644.2

(51) Int. Cl.
*A61K 38/43* (2006.01)
*C12N 9/88* (2006.01)
(52) U.S. Cl. ...................................... 424/94.1; 435/232
(58) Field of Classification Search .................. None
See application file for complete search history.

(56) References Cited

U.S. PATENT DOCUMENTS 6,815,194 B2 * 11/2004 Honjo et al. .................. 435/227
7,001,768 B2    2/2006 Wolffe

FOREIGN PATENT DOCUMENTS

| WO | 90/11354 | 10/1990 |
|---|---|---|
| WO | 9829108 | 7/1998 |
| WO | 0208286 | 1/2002 |
| WO | 03012051 | 2/2003 |
| WO | WO 03/095636 | * 11/2003 |
| WO | 2004/106550 | 12/2004 |

OTHER PUBLICATIONS

Altschul et al., 1997, Nucleic Acids Res., 25, pp. 3389-3402.
Barreto V, Reina-San-Martin B, Ramiro AR, McBride KM, Nussenzweig MC. C-terminal deletion of AID uncouples class switch recombination from somatic hypermutation and gene conversion Mol Cell. Aug. 2003;12(2):501-8.
Baylin SB. DNA methylation and gene silencing in cancer. Nat Clin Pract Oncol. Dec. 2005;2 Suppl 1:S4-11.
Di Noia, J.M., Rada, C., and Neuberger, M.S. (2006) SMUG1 is able to excise uracil from immunoglobulin genes: insight into mutation versus repair EMBO J 25, 585-595.
Egger G, Liang G, Aparicio A, Jones PA. Epigenetics in human disease and prospects for epigenetic therapy Nature May 2004; 429: 457-63.
Feinberg AP & Vogelstein B; Hypomethylation distinguishes genes of some human cancers from their normal counterparts Nature. 301; 89-92, Jan. 1983.
Fuks, F., Burgers, W. A., Godin, N., Kasai, M., and Kouzarides, T. (2001). Dnmt3a binds deacetylases and is recruited by a sequence-specific repressor to silence transcription EMBO J 20, 2536-2544.
Henikoff & Henikoff, 1992, Proc. Natl. Acad. Sci. USA, 89, pp. 10915.
Klein G. Epigenetics: surveillance team against cancer Nature (2005), 434(7030):150.
Morgan, H.D., Dean, W., Coker, H.A., Reik, W., and Petersen-Mahrt, S.K. (2004) Activation-induced cytidine deaminase deaminates 5-methylcytosine in DNA and is expressed in pluripotent tissues: implications for epigenetic reprogramming J Biol Chem 279, 52353-52360.
Murrell, A., Heeson, S., and Reik, W. (2004) Interaction between differentially methylated regions partitions the imprinted genes Igf2 and H19 into parent-specific chromatin loops Nat Genet 36, 889-893.
Muto T., Muramatsu M., Taniwaki M. Kinoshita K and Honjo T Isolation, tissue distribution, and chromosomal localization of the human activation-induced cytidine deaminase (AID) gene Genomics. Aug. 15, 2000;68(1):85-8.
Neuberger et al. Trends Biochem. Sci. (2003) 28:305-312.
Oswald, J., Engemann, S., Lane, N., Mayer, W., Olek, A., Fundele, R., Dean, W., Reik, W., and Walter, J. (2000) Active demethylation of the paternal genome in the mouse zygote Curr Biol, 10: 475-478.
Petersen-Mahrt, S. (2005) DNA deamination in immunity Immunol Rev 203, 80-97. Qin H. et al. (2007) Regulation of Apoptosis and Differentiation by p53 in Human Embryonic Stem Cells J. Biol. Chem., 282(8); 5842-5852.
Rada, C et al. Proc Natl Acad Sci U S A., May 14, 2002;99(10):7003-8.
Schoenherr C J, Levorse J M and Tilghman S. M. CTCF maintains differential methylation at the Igf2/H19 locus Nat. Genet. 2003; 33:66-69.
Ushijima T. Epigenetic field for Cancerization J. Bio. Mol. Biol. 2007; 40(2):142-150.
Wilmut I, Beaujean N, de Sousa PA, Dinnyes A, King TJ, Paterson LA, Wells DN, Young LE. Somatic cell nuclear transfer. Nature. Oct. 10, 2002, 419(6907); 583-6.
Yoo CB & Jones PA. Epigenetic therapy for cancer; part, present and future. Nature Review Drug Discovery Jan. 2006, 5: 37-50.
Lyko F, Brown R. DNA methyltransferase inhibitors and the development of epigenetic cancer therapies J Natl Cancer Inst. Oct. 19, 2005;97(20):1498-506.
International Search Report, PCT/GB2007/001304, dated Dec. 12, 2007.

(Continued)

*Primary Examiner* — Nashaat Nashed
(74) *Attorney, Agent, or Firm* — Lerner, David, Littenberg, Krumholz & Mentlik, LLP

(57) ABSTRACT

Demethylation of a methylated DNA sequence in a eukaryotic cell is described, utilizing a molecule that includes at least a first domain that exhibits a cytidine deaminase activity and at least a second domain that confers either a specific or non-specific DNA binding activity. The molecules of the invention are useful in somatic cell nuclear transfer and also in cancer therapy.

11 Claims, 6 Drawing Sheets

OTHER PUBLICATIONS

MacDuff et al, Molecular Immunology, 43; 1099-1108 (2006).
McBride et al., J. Exp. Med., 199(9); 1235-1244 (2004).
Bransteitter et al., Journal of Biological Chemistry, 279(49); 51612-51621 (2004).
Ito et al., PNAS, 101(7); 1975-1980 (2004).
Brar et al., Journal of Biological Chemistry, 279(25); 26395-26401 (2004).
Ta et al., Nature Immunology, 4(9); 843-848 (2003).
Chester et al., The EMBO Journal, 22(15); 3971-3982 (2003).
Yang et al., Experimental Cell Research, 267; 153-154 (2001).
Yang et al., Proc. Natl. Acad. Sci., 94; 13075-13080 (1997).
Dickerson et al. (2003) Journal of Experimental Medicine, 197 (10): 1291-1296.
Honjo et al. (2005) Nature Immunology, 6 (7): 655-61.
Besmer et al. (2006) Molecular and Cellular Biology, 26 (11): 4378-4385.
Navarro et al. (2005) Virology, 333: 374-386.
Yu et al. (2004) Nature Structural and Molecular Biology, 11(5): 435-442.

* cited by examiner

Figure 3 atggacagccttctgatgaagcaaaagaagtttctttaccatttcaaaaatgtccgctgg
gccaagggacggcatgagacctacctctgctacgtggtgaagaggagagatagtgccacc
tcctgctcactggacttcggccaccttcgcaacaagtctggctgccacgtggaattgttg
ttcctacgctacatctcagactgggacctggacccgggccggtgttaccgcgtcacctgg
ttcacctcctggagcccgtgctatgactgtgcccggcacgtggctgagtttctgagatgg
aaccctaacctcagcctgaggattttcaccgcgcgcctctacttctgtgaagaccgcaag
gctgagcctgaggggctgcggagactgcaccgcgctggggtccagatcgggatcatgacc
ttcaaagactattttactgctggaatacatttgtagaaaatcgtgaagaactttcaaa
gcctgggaagggctacatgaaaattct

Figure 4

CMV-GAL4-AidΔNES expression construct gacggatcggggagatctcccgatccctatggtcgactctcagtacaatctgctctgatgccgcatagttaagc
cagtatctgctccctgcttgtgtgttggaggtcgctgagtagtgcgcgagcaaaatttaagctacaacaaggca
aggcttgaccgacaattgcatgaagaatctgcttagggttaggcgttttgcgctgcttcgcgatgtacgggcca
gatatacgcgttgacattgattattgactagttattaatagtaatcaattacggggtcattagttcatagccca
tatatggagttccgcgttacataacttacggtaaatggcccgcctggctgaccgcccaacgaccccgcccatt
gacgtcaataatgacgtatgttcccatagtaacgccaatagggactttccattgacgtcaatgggtggactatt
tacggtaaactgcccacttggcagtacatcaagtgtatcatatgccaagtacgccccctattgacgtcaatgac
ggtaaatggcccgcctggcattatgcccagtacatgaccttatgggactttcctacttggcagtacatctacgt
attagtcatcgctattaccatggtgatgcggttttggcagtacatcaatgggcgtggatagcggtttgactcac
ggggatttccaagtctccaccccattgacgtcaatgggagtttgttttggcaccaaaatcaacgggactttcca
aatgtcgtaacaactccgccccattgacgcaaatgggcggtaggcgtgtacggtggaggtctatataagcag
agctctctggctaactagagaacccactgcttactggcttatcgaaattaatacgactcactatagggagaccc
aagctggnnnnnnATGAAGCTACTGTCTTCTATCGAACAAGCATGCGATATTTGCCGACTTAAAAAGCTCAAGTG
CTCCAAAGAAAAACCGAAGTGCGCCAAGTGTCTGAAGAACAACTGGGAGTGTCGCTACTCTCCCAAAACCAAAA
GGTCTCCGCTGACTAGGGCACATCTGACAGAAGTGGAATCAAGGCTAGAAAGACTGGAACAGCTATTTCTACTG
ATTTTTCCTCGAGAAGACCTTGACATGATTTTGAAAATGGATTCTTTACAGGATATAAAAGCATTGTTAACAGG
ATTATTTGTACAAGATAATGTGAATAAAGATGCCGTCACAGATAGATTGGCTTCAGTGGAGACTGATATGCCTC
TAACATTGAGACAGCATAGAATAAGTGCGACATCATCATCGGAAGAGAGTAGTAACAAAGGTCAAAGACAGTTG
ACTGTAAAGCTTGGTACCGAGCTC`GGATCC`atggacagccttctgatgaagcaaaagaagtttctttaccattt
caaaaatgtccgctgggccaagggacggcatgagacctacctctgctacgtggtgaagaggagagatagtgcca
cctcctgctcactggacttcggccaccttcgcaacaagtctggctgccacgtggaattgttgttcctacgctac
atctcagactgggacctggacccgggccggtgttaccgcgtcacctggttcacctcctggagcccgtgctatga
ctgtgcccggcacgtggctgagtttctgagatggaaccctaacctcagcctgaggattttcaccgcgcgcctct
acttctgtgaagaccgcaaggctgagcctgaggggctgcggagactgcaccgcgctggggtccagatcgggatc
atgaccttcaaagactattttactgctggaatacatttgtagaaaatcgtgaaagaactttcaaagcctggga
agggctacatgaaaattctg`gaattc`tgcagatatccatcacactggcggccgctcgagcatgcatctag `NruI` pcDNA3.1, including CMV promoter after NruI

Gal4 (in CAPITALS)

`EcoRI`

AidΔNES cDNA

`BamHI`

SEQUENCE LISTING

```
<160> NUMBER OF SEQ ID NOS: 9

<210> SEQ ID NO 1
<211> LENGTH: 507
<212> TYPE: DNA
<213> ORGANISM: Mus musculus

<400> SEQUENCE: 1
atggacagcc ttctgatgaa gcaaaagaag tttctttacc atttcaaaaa tgtccgctgg      60
gccaagggac ggcatgagac ctacctctgc tacgtggtga agaggagaga tagtgccacc     120
tcctgctcac tggacttcgg ccaccttcgc aacaagtctg gctgccacgt ggaattgttg     180
ttcctacgct acatctcaga ctgggacctg gacccgggcc ggtgttaccg cgtcacctgg     240
ttcacctcct ggagcccgtg ctatgactgt gcccggcacg tggctgagtt tctgagatgg     300
aaccctaacc tcagcctgag gattttcacc gcgcgcctct acttctgtga agaccgcaag     360
gctgagcctg aggggctgcg gagactgcac cgcgctgggg tccagatcgg gatcatgacc     420
ttcaaagact atttttactg ctggaataca tttgtagaaa atcgtgaaag aactttcaaa     480
gcctgggaag ggctacatga aaattct                                         507

<210> SEQ ID NO 2
<211> LENGTH: 1920
<212> TYPE: DNA
<213> ORGANISM: Artificial
<220> FEATURE:
<223> OTHER INFORMATION: Expression construct
<220> FEATURE:
<221> NAME/KEY: misc_feature
<222> LOCATION: (1)..(900)
<223> OTHER INFORMATION: pcDNA3.1 vector backbone
<220> FEATURE:
<221> NAME/KEY: misc_feature
<222> LOCATION: (206)..(211)
<223> OTHER INFORMATION: NruI restriction site
<220> FEATURE:
<221> NAME/KEY: CDS
<222> LOCATION: (901)..(1920)
<220> FEATURE:
<221> NAME/KEY: misc_feature
<222> LOCATION: (901)..(1362)
<223> OTHER INFORMATION: Gal4 coding sequence
<220> FEATURE:
<221> NAME/KEY: misc_feature
<222> LOCATION: (1357)..(1362)
<223> OTHER INFORMATION: BamHI restriction site
<220> FEATURE:
<221> NAME/KEY: misc_feature
<222> LOCATION: (1363)..(1876)
<223> OTHER INFORMATION: Aid mutant NES cDNA
```

```
<220> FEATURE:
<221> NAME/KEY: misc_feature
<222> LOCATION: (1871)..(1876)
<223> OTHER INFORMATION: EcoRI restriction site

<400> SEQUENCE: 2
```

| | | | | | |
|---|---|---|---|---|---|
| gacggatcgg | gagatctccc | gatcccctat | ggtcgactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacggggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggac | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccacccca | ttgacgtcaa | tgggagtttg | ttttggcacc | 720 |
| aaaatcaacg | ggactttcca | aaatgtcgta | acaactccgc | cccattgacg | caaatgggcg | 780 |
| gtaggcgtgt | acggtgggag | gtctatataa | gcagagctct | ctggctaact | agagaaccca | 840 |
| ctgcttactg | gcttatcgaa | attaatacga | ctcactatag | ggagacccaa | gctggnnnnn | 900 |

```
atg aag cta ctg tct tct atc gaa caa gca tgc gat att tgc cga ctt       948
Met Lys Leu Leu Ser Ser Ile Glu Gln Ala Cys Asp Ile Cys Arg Leu
1               5                   10                  15 aaa aag ctc aag tgc tcc aaa gaa aaa ccg aag tgc gcc aag tgt ctg       996
Lys Lys Leu Lys Cys Ser Lys Glu Lys Pro Lys Cys Ala Lys Cys Leu
            20                  25                  30 aag aac aac tgg gag tgt cgc tac tct ccc aaa acc aaa agg tct ccg      1044
Lys Asn Asn Trp Glu Cys Arg Tyr Ser Pro Lys Thr Lys Arg Ser Pro
        35                  40                  45 ctg act agg gca cat ctg aca gaa gtg gaa tca agg cta gaa aga ctg      1092
Leu Thr Arg Ala His Leu Thr Glu Val Glu Ser Arg Leu Glu Arg Leu
    50                  55                  60 gaa cag cta ttt cta ctg att ttt cct cga gaa gac ctt gac atg att      1140
Glu Gln Leu Phe Leu Leu Ile Phe Pro Arg Glu Asp Leu Asp Met Ile
65                  70                  75                  80 ttg aaa atg gat tct tta cag gat ata aaa gca ttg tta aca gga tta      1188
Leu Lys Met Asp Ser Leu Gln Asp Ile Lys Ala Leu Leu Thr Gly Leu
                85                  90                  95 ttt gta caa gat aat gtg aat aaa gat gcc gtc aca gat aga ttg gct      1236
Phe Val Gln Asp Asn Val Asn Lys Asp Ala Val Thr Asp Arg Leu Ala
            100                 105                 110 tca gtg gag act gat atg cct cta aca ttg aga cag cat aga ata agt      1284
Ser Val Glu Thr Asp Met Pro Leu Thr Leu Arg Gln His Arg Ile Ser
        115                 120                 125 gcg aca tca tca tcg gaa gag agt agt aac aaa ggt caa aga cag ttg      1332
Ala Thr Ser Ser Ser Glu Glu Ser Ser Asn Lys Gly Gln Arg Gln Leu
    130                 135                 140 act gta aag ctt ggt acc gag ctc gga tcc atg gac agc ctt ctg atg      1380
Thr Val Lys Leu Gly Thr Glu Leu Gly Ser Met Asp Ser Leu Leu Met
145                 150                 155                 160 aag caa aag aag ttt ctt tac cat ttc aaa aat gtc cgc tgg gcc aag      1428
Lys Gln Lys Lys Phe Leu Tyr His Phe Lys Asn Val Arg Trp Ala Lys
                165                 170                 175
```

-continued

```
gga cgg cat gag acc tac ctc tgc tac gtg gtg aag agg aga gat agt    1476
Gly Arg His Glu Thr Tyr Leu Cys Tyr Val Val Lys Arg Arg Asp Ser
            180                 185                 190 gcc acc tcc tgc tca ctg gac ttc ggc cac ctt cgc aac aag tct ggc    1524
Ala Thr Ser Cys Ser Leu Asp Phe Gly His Leu Arg Asn Lys Ser Gly
        195                 200                 205 tgc cac gtg gaa ttg ttg ttc cta cgc tac atc tca gac tgg gac ctg    1572
Cys His Val Glu Leu Leu Phe Leu Arg Tyr Ile Ser Asp Trp Asp Leu
    210                 215                 220 gac ccg ggc cgg tgt tac cgc gtc acc tgg ttc acc tcc tgg agc ccg    1620
Asp Pro Gly Arg Cys Tyr Arg Val Thr Trp Phe Thr Ser Trp Ser Pro
225                 230                 235                 240 tgc tat gac tgt gcc cgg cac gtg gct gag ttt ctg aga tgg aac cct    1668
Cys Tyr Asp Cys Ala Arg His Val Ala Glu Phe Leu Arg Trp Asn Pro
                245                 250                 255 aac ctc agc ctg agg att ttc acc gcg cgc ctc tac ttc tgt gaa gac    1716
Asn Leu Ser Leu Arg Ile Phe Thr Ala Arg Leu Tyr Phe Cys Glu Asp
            260                 265                 270 cgc aag gct gag cct gag ggg ctg cgg aga ctg cac cgc gct ggg gtc    1764
Arg Lys Ala Glu Pro Glu Gly Leu Arg Arg Leu His Arg Ala Gly Val
        275                 280                 285 cag atc ggg atc atg acc ttc aaa gac tat ttt tac tgc tgg aat aca    1812
Gln Ile Gly Ile Met Thr Phe Lys Asp Tyr Phe Tyr Cys Trp Asn Thr
    290                 295                 300 ttt gta gaa aat cgt gaa aga act ttc aaa gcc tgg gaa ggg cta cat    1860
Phe Val Glu Asn Arg Glu Arg Thr Phe Lys Ala Trp Glu Gly Leu His
305                 310                 315                 320 gaa aat tct gga att ctg cag ata tcc atc aca ctg gcg gcc gct cga    1908
Glu Asn Ser Gly Ile Leu Gln Ile Ser Ile Thr Leu Ala Ala Ala Arg
                325                 330                 335 gca tgc atc tag                                                    1920
Ala Cys Ile
```

<210> SEQ ID NO 3
<211> LENGTH: 339
<212> TYPE: PRT
<213> ORGANISM: Artificial
<220> FEATURE:
<223> OTHER INFORMATION: Synthetic Construct

<400> SEQUENCE: 3

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Asn Lys Gly Gln Arg Gln Leu
    130                 135                 140
```

Thr Val Lys Leu Gly Thr Glu Leu Gly Ser Met Asp Ser Leu Leu Met
145                 150                 155                 160

Lys Gln Lys Lys Phe Leu Tyr His Phe Lys Asn Val Arg Trp Ala Lys
            165                 170                 175

Gly Arg His Glu Thr Tyr Leu Cys Tyr Val Val Lys Arg Arg Asp Ser
        180                 185                 190

Ala Thr Ser Cys Ser Leu Asp Phe Gly His Leu Arg Asn Lys Ser Gly
    195                 200                 205

Cys His Val Glu Leu Leu Phe Leu Arg Tyr Ile Ser Asp Trp Asp Leu
210                 215                 220

Asp Pro Gly Arg Cys Tyr Arg Val Thr Trp Phe Thr Ser Trp Ser Pro
225                 230                 235                 240

Cys Tyr Asp Cys Ala Arg His Val Ala Glu Phe Leu Arg Trp Asn Pro
                245                 250                 255

Asn Leu Ser Leu Arg Ile Phe Thr Ala Arg Leu Tyr Phe Cys Glu Asp
            260                 265                 270

Arg Lys Ala Glu Pro Glu Gly Leu Arg Arg Leu His Arg Ala Gly Val
        275                 280                 285

Gln Ile Gly Ile Met Thr Phe Lys Asp Tyr Phe Tyr Cys Trp Asn Thr
290                 295                 300

Phe Val Glu Asn Arg Glu Arg Thr Phe Lys Ala Trp Glu Gly Leu His
305                 310                 315                 320

Glu Asn Ser Gly Ile Leu Gln Ile Ser Ile Thr Leu Ala Ala Ala Arg
                325                 330                 335

Ala Cys Ile

<210> SEQ ID NO 4
<211> LENGTH: 25
<212> TYPE: DNA
<213> ORGANISM: Artificial
<220> FEATURE:
<223> OTHER INFORMATION: primer

<400> SEQUENCE: 4
gtaagatgtg tgtattttg gaatg                                    25

<210> SEQ ID NO 5
<211> LENGTH: 25
<212> TYPE: DNA
<213> ORGANISM: Artificial
<220> FEATURE:
<223> OTHER INFORMATION: primer

<400> SEQUENCE: 5
aatccctaac ttctcctaat ctcta                                   25

<210> SEQ ID NO 6
<211> LENGTH: 24
<212> TYPE: DNA
<213> ORGANISM: Artificial
<220> FEATURE:
<223> OTHER INFORMATION: primer

<400> SEQUENCE: 6
gtaagatgtg tgtattttg gaat                                     24

<210> SEQ ID NO 7
<211> LENGTH: 26
<212> TYPE: DNA
<213> ORGANISM: Artificial

```
<220> FEATURE:
<223> OTHER INFORMATION: F2 reverse primer

<400> SEQUENCE: 7
caaccaaact aacttaacta caaatc                                              26

<210> SEQ ID NO 8
<211> LENGTH: 20
<212> TYPE: DNA
<213> ORGANISM: Artificial
<220> FEATURE:
<223> OTHER INFORMATION: Gal4 region primer

<400> SEQUENCE: 8
aagtgcgcca agtgtctgaa                                                     20

<210> SEQ ID NO 9
<211> LENGTH: 20
<212> TYPE: DNA
<213> ORGANISM: Artificial
<220> FEATURE:
<223> OTHER INFORMATION: Aid region primer

<400> SEQUENCE: 9
cagccagact tgttgcgaag                                                     20
```

COMPOSITIONS AND METHOD FOR EPIGENETIC MODIFICATION OF NUCLEIC ACID SEQUENCES IN VIVO

This application is a national stage application of PCT/GB2007/001304 filed on Apr. 10, 2007 which claims the benefit of priority to GB 0607063.5 filed on Apr. 7, 2006, U.S. 60/790,273 filed on Apr. 7, 2006, U.S. 60/797,942 filed on May 5, 2006, GB 0623644.2 filed on Nov. 27, 2006 the contents of which are incorporated herein by reference.

FIELD

The invention relates to the field of epigenetic modification of genomic DNA in animal cells. In particular, methods and compositions for controlling methylation of genomic DNA in mammalian cells.

BACKGROUND

Epigenetics concerns the transmission of information from a cell or multicellular organism to its descendants without that information being encoded in the nucleotide sequence of genes. One mechanism by which epigenetic information is transmitted is via methylation of cytosine (C) bases in the genomic DNA of multicellular organisms.

DNA methylation in multicellular organisms occurs mainly at CpG dinucleotides, and has important regulatory functions in development and in the epigenetic control of gene expression, including genomic imprinting, X chromosome inactivation, the silencing of transposable elements, and possibly wider roles in silencing of genes in development. Loss of DNA methylation can occur during DNA replication by inactivation of the major maintenance methyltransferase Dnmt1. In addition, there are a number of examples in mammals and plants where demethylation occurs without replication of DNA, and hence is likely to be an active enzymatic process.

Active demethylation of DNA is thought to occur in a variety of biological systems in animals and plants, but the molecular mechanisms are not yet understood. In *Arabidopsis*, the DNA glycosylase Demeter has been shown to excise 5-methylcytosine from DNA and to be required for the activation of the maternal allele of Medea, an imprinted gene.

In cancer, it is well documented that the majority of tumour cells display abnormal DNA epigenetic imprints (Feinberg and Vogelstein, 1983). Studies have gone on to show that tumour suppressor genes within cancer cells are silenced by DNA methylation (Lyko and Brown, 2005). In gastric cancers, inactivation of the genes CDKN2A, CDH1, hMLH1 and RUNX3 has been described as resulting from DNA methylation in their respective promoters and it is believed that these and other genes may be methylated in response to infection by *Helicobacter pylori* (Ushijima, 2007).

Cancer is the second leading cause of death in the United States. An estimated 10.1 million Americans are living with a previous diagnosis of cancer. In 2002, 1,240,046 people were diagnosed with cancer in the United States (information from Centres for Disease Control and Prevention, 2004 and 2005, and National Cancer Institute, 2005). By way of example, according to Cancer Research UK, almost 44,100 cases of breast cancer are diagnosed in the UK each year (i.e. 16% of all new cancer cases), and over 12,400 deaths result annually from this disease in the UK. In the same period almost 7,000 new cases of pancreatic cancer are diagnosed in the UK (3% of all new cases), and approximately the same number of deaths result. An appreciation of why and how epigenetic changes are regulated is critical to the understanding, detection and treatment of cancer.

Methylation and resultant gene silencing plays an important role in cancer development and also in cancer progression. Reversal of the aberrant methylation patterns induced in cancer cells represents a way in which types of cancers that are poorly responsive to conventional chemotherapeutic treatments could be targeted. In addition, epigenetic treatment factors that target DNA methylation could also be used to treat advanced or inoperable cancers, or as a adjunct to other conventional existing therapies.

Somatic cell nuclear transfer (SCNT) is used to generate animals for livestock production (for cloning or for stem cell therapy), biomanufacturing of proteins and for disease modelling (Wilmut et al, 2002). A major obstacle to the application of SCNT in order to reprogramme somatic donor nuclei to a pluripotent state is the inefficient demethylation of the donor genome by the recipient oocyte. It has been found that genomic patterns of DNA methylation are reprogrammed genome-wide in early embryos and in primordial germ cells. The ability to manipulate in a targeted fashion epigenetic reprogramming in vivo may thus have important applications in regenerative medicine and in cancer therapy.

Several possible biochemical pathways for demethylation have been suggested, but until recently none of these has been proved to operate in vivo. In vitro studies in *E. coli* have shown that the cytidine deaminases Activation induced cytidine deaminase (Aid) and Apobec1 can deaminate 5-methylcytosine in DNA (Morgan et al 2004). This deamination results in a thymine base opposite a guanine, which may be repaired to a cytosine via endogenous DNA mismatch repair mechanisms, leading to effective demethylation. In the event that mismatch repair does not occur the deamination can cause transition mutations.

The role of Aid in antibody gene diversification and somatic hypermutation (SMH), via deamination of cytosines in specific regions of the immunoglobulin locus, has been previously characterised (Neuberger et al. 2003). In the organism, Aid is usually located in the cytoplasm where it is tightly regulated (Rada et al. 2002). It is believed that Aid activity is moderated by interactions with other proteins in the cell. Thus, it is generally thought that, in vivo, Aid is tightly controlled because an 'unregulated' deamination activity would be potentially hazardous to the cell since it could result in an increased rate of mutation in the genome and/or activation of epigenetically silenced genes.

It is apparent, therefore, that there is a need for novel compositions and methods that provide for either global or directed demethylation of genomic DNA in animal cells, optionally mammalian somatic cells, whilst maintaining the integrity of the sequence of that DNA.

SUMMARY

In a first aspect, the invention provides an isolated polypeptide molecule capable of initiating a demethylation of a methylated DNA sequence in a eukaryotic cell, the molecule comprising at least a first domain that exhibits a cytidine deaminase activity and at least a second domain that confers a DNA binding activity. In a specific embodiment the molecule of the invention, further comprises a nuclear localisation signal, which may or may not be comprised within the first domain. Suitably the first domain comprises the cytidine deaminase domain of an Activation induced cytidine deaminase (Aid). In a specific embodiment, the first domain comprises the AidΔNES sequence set out in SEQ ID NO: 1. Alternatively, the first domain comprises the cytidine deaminase domain of Apobec1.

In particular embodiments of the invention, the second domain comprises either a non-sequence specific DNA binding domain, or a sequence specific DNA binding domain. Where a sequence specific DNA binding domain is selected it may comprise a domain selected from: a zinc finger domain; a leucine zipper domain; a helix-turn-helix domain; a steroid receptor DNA binding domain; and a homeodomain. Optionally, the sequence specific DNA binding domain is targeted to a bind sequence present in the promoter region of one or more genes whose expression is associated with a pluripotent phenotype. Suitably, the sequence specific DNA binding domain is targeted to a bind sequence present in the promoter region of one or more genes whose expression is associated with a tumour suppression phenotype.

In a specific embodiment of the invention the cell is a mammalian cell, optionally a human cell. In further embodiments of the invention the cell can be a pluripotent cell, a somatic cell or a cancer cell.

A second aspect of the invention provides for an isolated nucleic acid molecule that encodes a polypeptide molecule as described in any of the embodiments mentioned above.

A third aspect of the invention provides for an expression vector for transfection of, and expression within a eukaryotic cell of, a polypeptide molecule capable of initiating a demethylation of a methylated DNA sequence in the cell, the vector comprising a coding sequence that includes a first nucleic acid sequence that encodes a polypeptide sequence that exhibits a cytidine deaminase activity, the first sequence being linked to at least a second nucleic acid sequence that encodes a polypeptide sequence that confers a DNA binding activity, the first and second nucleic acid sequences being operably linked to a promoter sequence.

A fourth aspect of the invention provides a nucleic acid vector for transfection of a eukaryotic cell, the vector comprising a sequence that encodes a molecule that is capable of initiating demethylation of methylated genomic DNA within the mammalian cell, the vector comprising a first nucleic acid sequence that encodes a polypeptide that exhibits a cytidine deaminase activity linked to a second nucleic acid sequence that encodes a polypeptide sequence that exhibits a DNA binding activity, the first, and second sequences being operably linked to a promoter sequence.

In embodiments of the invention the vectors further comprise one or more selection marker sequences and/or reporter gene sequences. In a specific embodiment of the invention, the first and second nucleic acid sequences are separated by one or more intervening sequences. Optionally, the promoter sequence is selected from either a constitutive promoter or an inducible promoter. In an embodiment of the invention, the inducible promoter is selected from: a Tet regulated promoter; a Tamoxifen regulated promoter; and a steroid hormone regulated promoter. Suitably, the vectors further comprise a sequence that encodes a nuclear localisation signal. In a specific embodiment the vectors of the invention comprise a nucleic acid molecule that encodes a polypeptide of the invention. Suitably, the vectors are selected from: a plasmid; a cosmid; a viral vector; and an artificial chromosome. Typically, vectors are suitable for use in a mammalian cell, optionally a human cell. In specific embodiments, the cell is a pluripotent cell, a somatic cell, and/or a cancer cell.

Further aspects of the invention provide methods for initiating demethylation of a methylated DNA sequence in a target cell, comprising transfecting the target cell with a vector described above and, if required, initiating expression of the vector within the target cell. Typically, the demethylation of the DNA sequence is for the purpose of removing epigenetic imprints in the genome of the target cell.

A further aspect of the invention provides a method for undertaking a somatic cell nuclear transplant (SCNT) procedure comprising expressing within a somatic cell nuclear donor a polypeptide molecule capable of initiating a demethylation of at least one methylated DNA sequence located in the genome of the somatic cell, the molecule comprising at least a first domain that exhibits a cytidine deaminase activity and at least a second domain that confers a DNA binding activity.

A still further aspect of the invention provides a method for treating cancer present within a patient, comprising expressing within at least one cancer cell in the patient, a polypeptide molecule capable of initiating a demethylation of at least one methylated DNA sequence located in the genome of the cancer cell, the molecule comprising at least a first domain that exhibits a cytidine deaminase activity and at least a second domain that confers a DNA binding activity.

In a further aspect the invention provides for a transgenic non-human animal that comprises a nucleic acid molecule of the invention that is stably integrated within the genome of the non-human animal. Typically, expression of the nucleic acid molecule is under the control of a heterologous inducible promoter. Although, in an embodiment of the invention, expression of the nucleic acid molecule is under the control of an endogenous inducible promoter. In a specific embodiment, the non-human animal is a mouse.

A further aspect of the invention provides a pharmaceutical composition comprising a polypeptide or nucleic acid molecule described above and a pharmaceutically acceptable carrier.

The methods and compositions of the invention are suitable for use in animal cells, suitably mammalian cell systems. The invention is intended to be worked in human cells, although it should be appreciated that the invention is in no way intended to encompass reproductive cloning of human beings.

These and other uses, features and advantages of the invention should be apparent to those skilled in the art from the teachings provided herein.

b) shows the differentially methylated region (DMR) upstream of H19 and the position into which the UAS sequence was inserted (a single loxP site is also present as a result of the recombination strategy). If this genotype is combined with the CMV-Gal4-AidΔNES (SEQ ID NO:2) transgene in offspring of CMV-Gal4-AidΔNES (SEQ ID NO:2) mothers with H19 DMR UAS fathers, the Gal4-AidΔNES fusion protein (SEQ ID NO:3) will bind to the UAS sequence on the paternal methylated (closed lollipops) allele. The regions analysed by bisulphite sequencing are shown above the chromosomes as Bi1 and Bi2.

Figure 1:
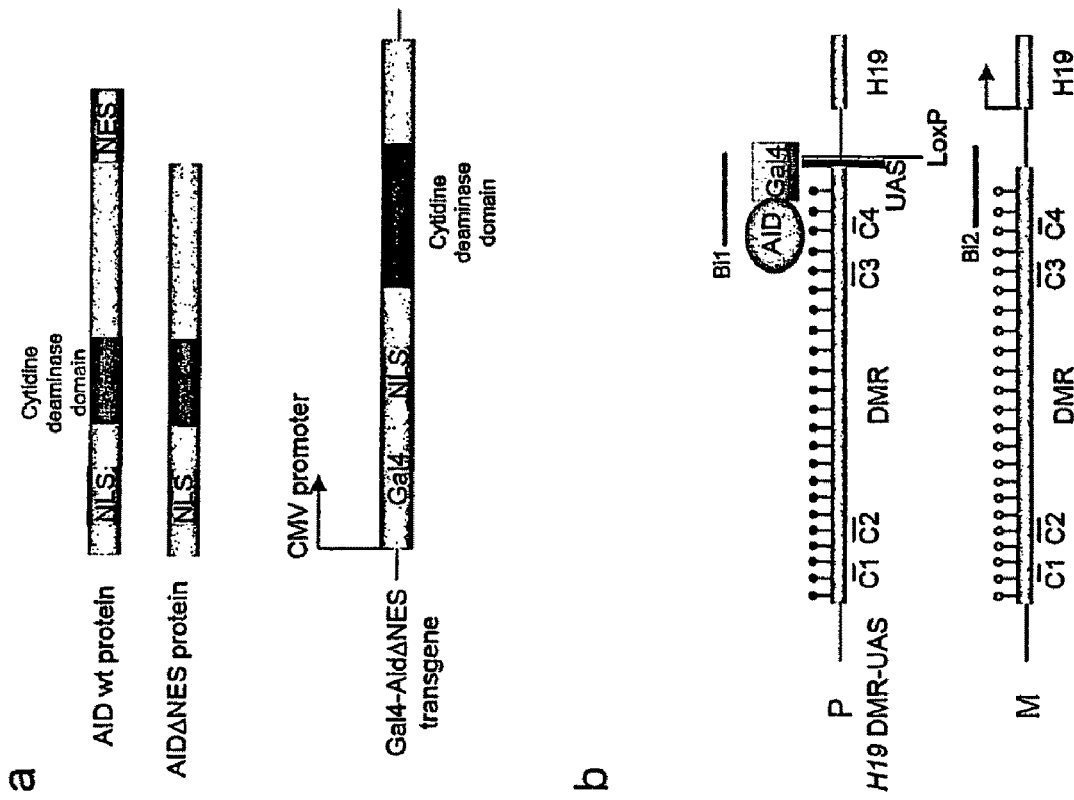
FIG. 1 shows the structure of the transgene producing the fusion protein Gal4-Aid, and schematic of the transgenic targeting strategy in vivo a) structure of the Aid protein, the Aid protein variant with a C terminal deletion that removes the nuclear export signal (AidΔNES), and the transgene that expresses a Gal4-deleted AidΔNES fusion protein from a CMV promoter (SEQ ID NO:2).
Figure 2:
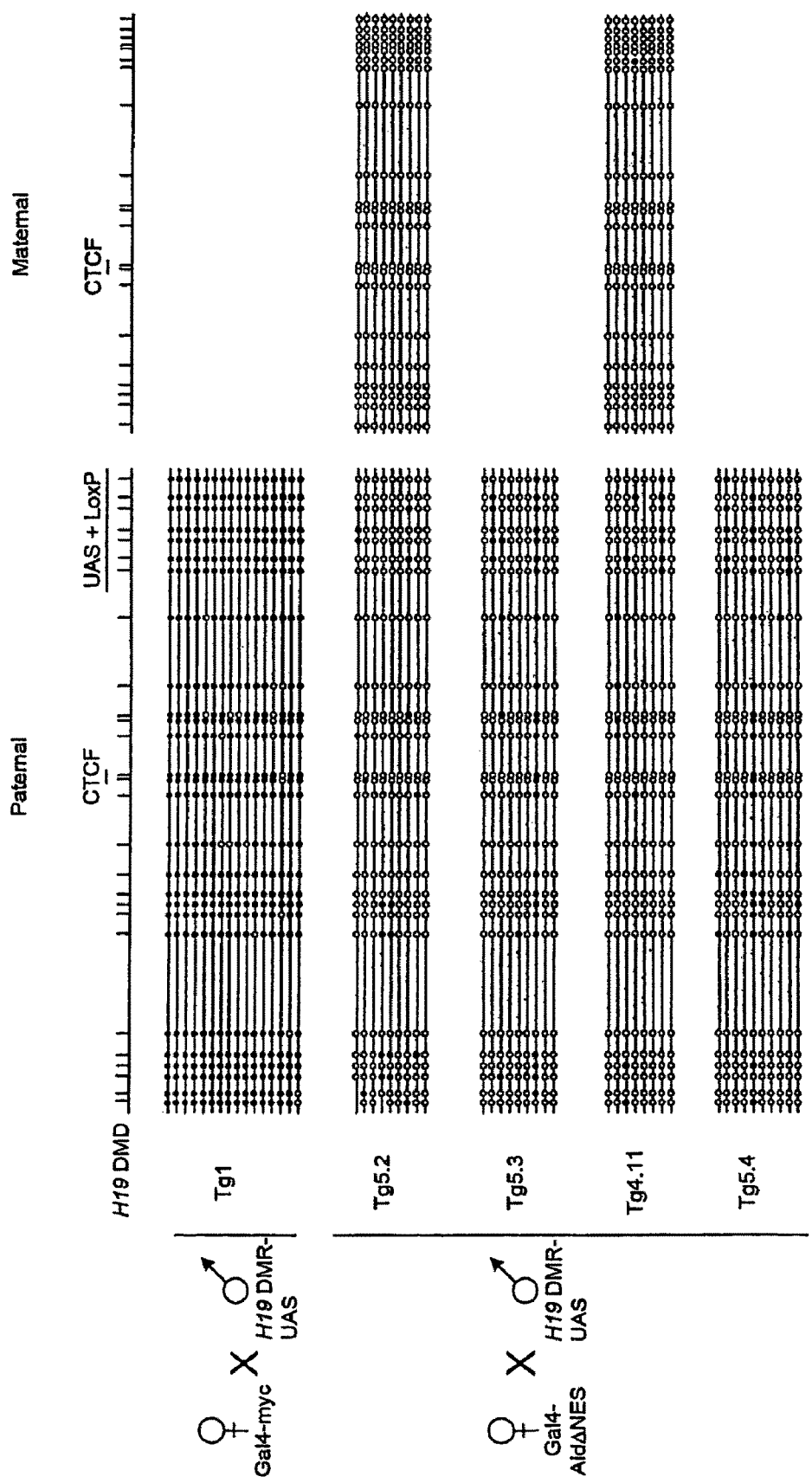

FIG. 2 shows a methylation analysis of the H19 DMR in experimental and control crosses; bisulphite analysis of the region indicated in FIG. 1 was carried out on neonatal livers of offspring from crosses between CMV Gal4-myc females and H19 DMR UAS males (control) and from CMV Gal4-AidΔNES (SEQ ID NO:2) females and H19 DMR UAS males. Closed circles, methylated CpGs, open circles, unmethylated circles. The paternal H19 DMR UAS is highly methylated in the control cross, but substantially hypomethylated in the experimental one. Maternal chromosomes are unmethylated in both crosses.

FIG. 3 shows the sequence of AidΔNES (SEQ ID NO:1).

FIG. 4 shows the sequence of the CMV-GAL4-AidΔNES (SEQ ID NO:2).

Figure 5:
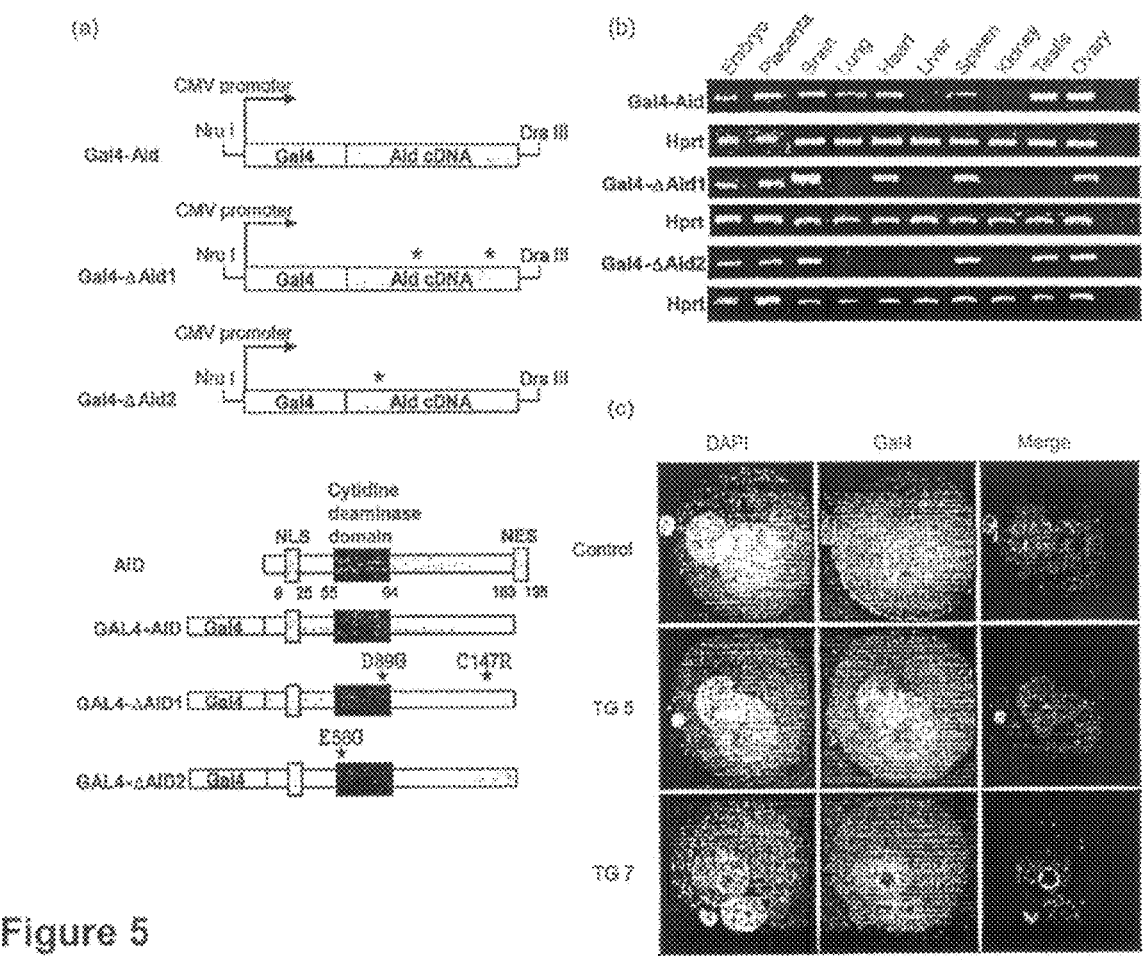

FIG. 5 shows a, The Gal4 DNA binding domain was fused to the Aid cDNA from which the C terminus containing the nuclear export signal (NES) was deleted. Amino acids in Aid are numbered. In addition to the wildtype Aid cDNA two mutant forms of Aid cDNA, resulting in amino acid changes D89G and C147R, and E58G, respectively, were used. Insertion of fusion cDNAs into a CMV promoter vector resulted in three transgene constructs, which were excised from the plasmid backbone with NruI and DraIII and microinjected into zygotes, resulting in transgenic strains TG4 and 5 (CMV Gal4-AidΔNES (SEQ ID NO:2)—shown here simply as 'CMV Gal4-Aid' (SEQ ID NO:2)), TG7 (CMV Gal4-ΔAid1), and TG8 (CMV Gal4-ΔAid2). b, Expression analysis of strains TG5, TG7, and TG8 by RT PCR in embryonic and neonatal tissues. c, Expression analysis of strains TG5 and TG7 by immunofluorescence with Gal4 DNA binding domain antibody in zygotes (transgenic mother times H19 DMR-UAS father). The fusion proteins are predominantly localised in the pronuclei.

Figure 6:
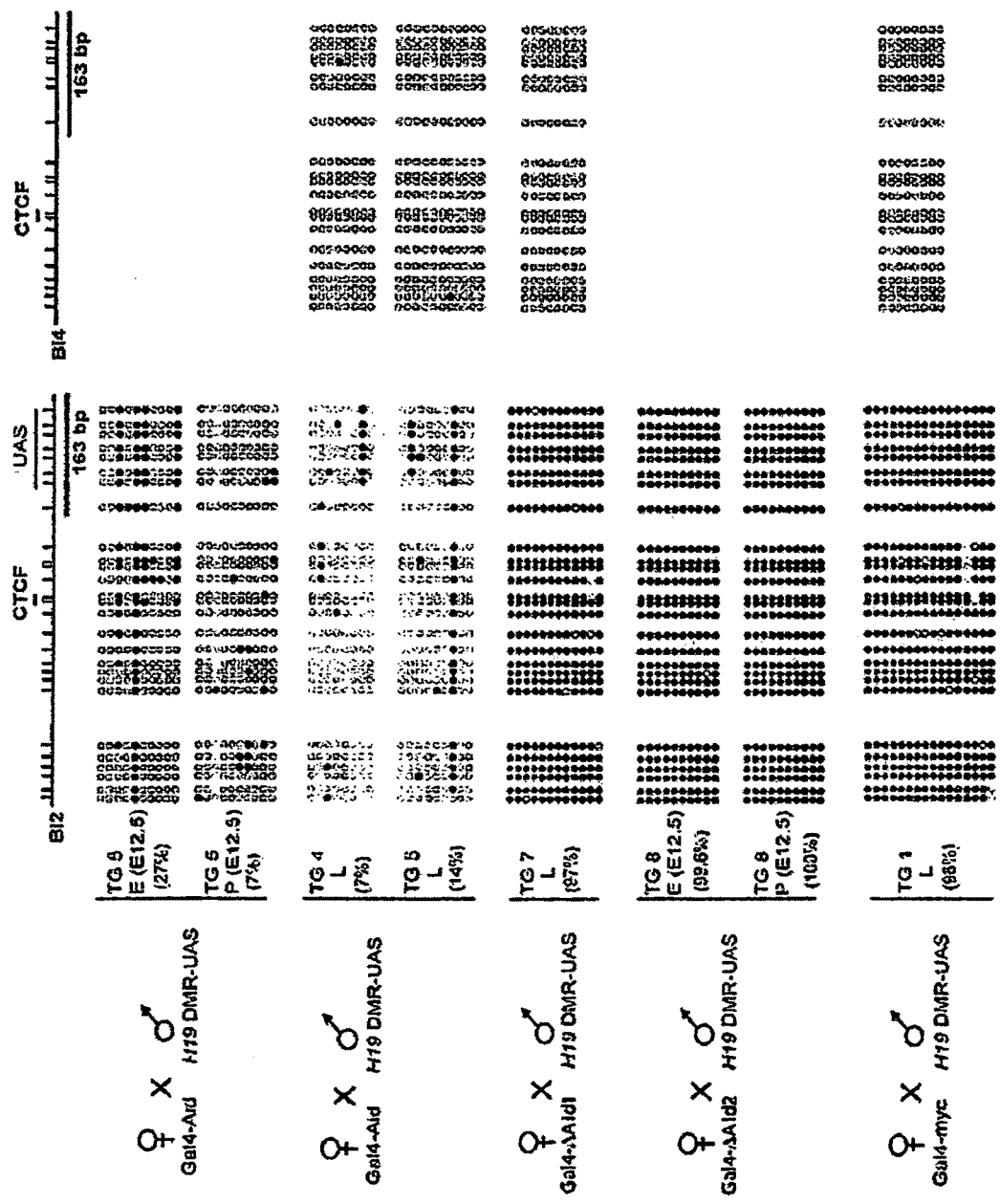

FIG. 6 shows methylation in the H19 DMR-UAS as analysed by bisulphite sequencing on the paternal allele which contains the UAS sequence (left panel), and on the maternal allele which does not (right panel). Gal4 transgenic females were crossed with H19 DMR-UAS homozygous males, and methylation was analysed in embryos (E) and placentas (P) at E12.5, or in neonatal liver (L), of transgene positive offspring. Filled circles=methylated CpGs, open circles, =unmethylated CpGs. The 4th CTCF binding site within the DMR is shown. The paternal DMR remains highly methylated in strains expressing Gal4-myc or the Gal4-Aid mutants, but is substantially demethylated in strains expressing Gal4-AidΔ-NES (SEQ ID NO:2) (shown here simply as Gal4-Aid).

DETAILED DESCRIPTION

Prior to setting forth the invention, a number of definitions are provided that will assist in the understanding of the invention. All references cited herein are incorporated by reference in their entirety. Unless otherwise defined, all technical and scientific terms used herein have the same meaning as commonly understood by one of ordinary skill in the art to which this invention belongs.

The term 'reprogramming' as used herein, refers to the step of modifying or removing epigenetic imprints from the nucleus of a cell. Reprogramming facilitates a reduction in cell fate commitment and, thus, the differentiation state of the cell as a whole and in particular the nucleus. In essence, reprogramming consists of returning a somatic differentiated or committed nucleus to a gene expression, epigenetic, and functional state characteristic of an embryonic, germ, or stem cell. Reprogramming of somatic cell nuclei is a preferred first step in procedures such as SCNT, but is also of interest in other procedures where control of cell differentiation state—i.e. potency—is important.

The term 'imprinting' refers to the "memory" held by a chromosome as to which parent it was inherited from. This memory is brought about by epigenetic marks, including DNA methylation, chemically imprinted onto the DNA and can result in chromosomes behaving differently, depending on the parent of origin. Parent-of-origin-specific gene expression (either from the maternal or paternal chromosome) is often observed in mammals. This is in the parental germlines, which lead to stable gene silencing or activation.

The term DNA methylation' refers to the addition of a methyl ($CH_3$) group to a specific base in the DNA. In mammals, methylation occurs almost exclusively at the 5 position on a cytosine when this is followed by a guanine (CpG). DNA methylation acts as an epigenetic mark, which has important roles in regulating genome function and expression.

Cytidine deaminases are a family of enzymes found from prokaryotic organisms such as *E. coli* through to mammals. These enzymes deaminate the free cytidine or the cytosine in DNA or RNA to uracil, or as shown for Aid and Apobec1 (two members of the family) the methylated cytosine to thymine.

The term DNA mismatch repair' refers to a repair process present in the cell of a host organism that recognises and corrects base pairs in DNA that are mismatched, i.e. deviate from the normal C:G and A:T Watson-Crick DNA base pairing rules.

The term 'cancer' is used herein to denote a tissue or a cell located within a neoplasm or with properties associated with a neoplasm. Neoplasms typically possess characteristics that differentiate them from normal tissue and normal cells. Among such characteristics are included, but not limited to: a degree of anaplasia, changes in cell morphology, irregularity of shape, reduced cell adhesiveness, the ability to metastasise, increased levels of angiogenesis, increased cell invasiveness, reduced levels of cellular apoptosis and generally increased cell malignancy. Terms pertaining to and often synonymous with 'cancer' include sarcoma, carcinoma, tumour, epithelioma, leukaemia, lymphoma, polyp, transformation, neoplasm and the like.

'Bioprocessing' refers to techniques in which living cells, or their components are used to produce a desired end product. In the context of the present invention, epigenetic modifications to cells can be used to enhance these cells ability to be used in bioprocessing. For instance, targeted demethylation of the genome can be used to improve efficiency of cloned animal production via SCNT, where the cloned animals are transgenic and produce a desired end product.

Somatic cells typically develop along a differentiation pathway progressing from a less specialised to a more specialised or committed state. Less specialised somatic cells can demonstrate the ability to act as progenitor stem cells giving rise to several different cell types. The amount of these different cell types that a given stem cell can act as a progenitor for is typically referred to as the 'potency' of that stem cell. Hence, pluripotent stem cells can act as progenitors for very many different differentiated cell types. If a cell can differentiate into all cells in the body, it is totipotent. If it can differentiate into most cell types, it is pluripotent. Embryonic stem cells are usually referred to as pluripotent as they can generate most cell types in mammals with the exception of extraembryonic tissues (i.e. trophectoderm).

The terms 'derivative or homologues' of Aid as used herein refer to mRNA and polypeptides that have substantially similar sequence identity to that of human or murine Aid. Derivatives and homologues are considered to include orthologues of the sequences from other species and mutants that nonetheless exhibit a high level of functional equivalence—i.e. cytidine deaminase activity in vivo. By substantially similar sequence identity, it is meant that the level of sequence identity is from about 50%, 60%, 70%, 80%, 90%, 95% to about 99% identical. Percent sequence identity can be determined using conventional methods (e.g. Henikoff & Henikoff, 1992; and Altschul et al., 1997). It will be appreciated that the level of sequence identity described herein refers to both polypeptide sequences and polynucleotide sequences (DNA or RNA). Alternatively, homologues of the cytidine deaminase domains—e.g. AidΔNES (SEQ ID NO:1)—can be those sequences that are able to demonstrate the ability to hybridise with the Aid sequences described herein, under conditions of high, medium or low stringency.

A "polypeptide" is a polymer of amino acid residues joined by peptide bonds, whether produced naturally or in vitro by synthetic means. Polypeptide of less than approximately 12 amino acid residues in length is typically referred to as a "peptide". The term "polypeptide" as used herein denotes the product of a naturally occurring polypeptide, precursor form or proprotein. Polypeptides also undergo maturation or post-translational modification processes that may include, but are not limited to: glycosylation, proteolytic cleavage, lipidization, signal peptide cleavage, propeptide cleavage, phosphorylation, and such like. A "protein" is a macromolecule comprising one or more polypeptide chains.

The term "promoter" as used herein denotes a region within a gene to which transcription factors and/or RNA polymerase can bind so as to control expression of an associated coding sequence. Promoters are commonly, but not always, located in the 5' non-coding regions of genes, upstream of the translation initiation codon. The promoter region of a gene may comprise one or more consensus sequences that act as recognisable binding sites for sequence specific DNA binding domains of DNA binding proteins. Nevertheless, such binding sites may also be located in regions outside of the promoter, for example in enhancer regions located in introns or downstream of the coding sequence.

All references cited herein are incorporated by reference in their entirety. Unless otherwise defined, all technical and scientific terms used herein have the same meaning as commonly understood by one of ordinary skill in the art to which this invention belongs.

In a primary embodiment, the present invention resides in part in the identification of a modified form of a cytidine deaminase, termed AidΔNES (SEQ ID NO:1), that when expressed in mammalian cells leads to demethylation of imprinted regions within the genome. The modified form of Aid lacks a nuclear export signal (ΔNES) and as a result when heterologously expressed in cells the enzyme remains localised to the nuclei of the cells, whereas wild type Aid would be usually found mainly in the cytoplasm. The present C terminal truncation is novel and more extensive than that performed previously. C terminal truncations of Aid have previously been shown to have effects on nuclear export and that these abolish class switch recombination (CSR) but not somatic hypermutation (SHM) (Barreto et al. 2003). Hence, in its broadest conception, the present invention provides for compositions and molecules possessing nuclear localised cytidine deaminase activity combined with a DNA binding activity, that show widespread utility in bioprocessing and cancer treatment amongst other uses.

According to an embodiment of the present invention, a fusion of AidΔNES and the GAL4 DNA binding protein (SEQ ID NO:3) bound to a UAS sequence placed upstream of the H19 gene in mouse cells and resulted in demethylation of cytidine residues in a DMR up to approximately 600 bases on either side of the UAS. The demethylation of this region results in switching on of H19 gene expression. Sequencing of the promoter sequence afterwards indicated that the level of mismatch point mutation was not increased to statistically significant levels. This is an important and surprising result, as Aid is a deaminase and relies essentially on host excision repair mechanism to correct the T-G mismatch following the deamination of the methylated C to a T. There are currently no known single function demethylase enzymes, hence, Aid represents a part of a notional 'demethylase' function characterised by deamination of methylcytosine followed by excision repair by the host's own mechanisms. It is believed that this is the first time that the Aid mediated demethylation of DNA has been shown to work in-vivo and in a targeted manner.

In an example of the invention in use, set out in more detail below, the in vivo experiments have been carried out in a mouse model. However, the results are readily applicable to other mammalian species including, other rodents, cattle, sheep, goats, pigs, primates and humans. At 92% identical at amino acid level, there is a high level of conservation between murine Aid (GENBANK accession no: NM_009645) and its human homologue (GENBANK accession no: AB040430) (Muto et al., 2000). Moreover, the DNA mismatch repair mechanisms employed in human and mouse are known to be highly comparable.

The present invention has demonstrated a number of important factors. First, it shows that local targeting of a cytidine deaminase activity, such as that of Aid or Apobec, to a methylated region in the genome in vivo can lead to its efficient demethylation without causing potentially catastrophic point mutations. Second, it demonstrates that full methylation in a DMR of an imprinted gene can be erased by an enzymatic mechanism; such erasure normally occurs during the development of primordial germ cells at E11.5 to E12.5 (in the mouse model) and may also involve active demethylation.

A role for both epigenetic (DNA methylation) and genetic (mutations) actions of cytidine deaminases in cancer has been proposed, and a possible role in demethylation which is widespread and may be an early event in cancer appears to be further strengthened by the present results.

The current system has been shown to work in a transgenic system, whereby expression in mice of a Gal4-AidΔNES fusion gene (SEQ ID NO:2) together with a UAS (Gal4-binding site) into a methylated region (H19 DMR) results in its demethylation, without apparent mutations. The suggested mechanism is by deamination of 5 methylcytosine by Aid to T, followed by T:G mismatch repair (by mismatch glycosylases). This therefore establishes a system by which methylated genes can be targeted for demethylation in vivo, which may lead to their expression (methylation being a repressive modification most of the time).

The model system exemplified in the present example relies on the fact that the target gene in question (H19) has been modified by addition of a UAS sequence, to its promoter region. However, this is not a requirement of the embodiments of the present invention which can also work by using fusions of a cytidine deaminase domain, for example AidΔNES, to specific or non-specific DNA binding domains, for example, zinc finger proteins that have specific DNA binding properties or simply protein domains with a net positive charge that favour non-specific DNA binding.

The presence of a site specific DNA binding domain allows for targeted demethylation of specific subsets of genes activated at particular times in development or during the cell cycle. For instance, the DNA binding domains of the Oct4, SOX-2 or Nanog proteins when fused to AidΔNES (SEQ ID NO:1) could provide for a demethylation activity that is directed towards genes that are involved in cell fate decisions relating to promotion of a pluripotent or stem cell-like phenotype. Alternative DNA binding domains that could optionally be utilised include those from T-box transcription factors such as Brachyury, or steroid hormone receptor DNA binding domains such as the RAR and RXR DNA binding domains. Nevertheless, AidΔNES (SEQ ID NO:1) expression alone (without targeting domain) could be also sufficient to demethylate the promoters of the pluripotent marker genes Oct4 and Nanog as it has been found that there are several putative binding sites for Aid itself in the upstream regions of these genes.

If non-specific targeting of demethylation is required the cytidine deaminase domain is suitably fused to a protein domain of net positive charge—for example, comprising a histone tail sequence from histones H2A/B, H3 and/or H4. Custom peptide sequences that permit non-specific DNA binding can also be incorporated, in accordance with this embodiment of the invention.

Cytidine deaminase activity combined with DNA binding, in accordance with the embodiments of the invention, is therefore an epigenetic reprogramming, or imprint erasure, factor. The identification of such factors is of great interest for the improvement of somatic cell nuclear transfer techniques (cloning), stem cells and regenerative medicine, and certain approaches to cancer therapy. Indeed, according to the Examples of the present invention in use (see below) it is clear that exposure of a fully methylated H19 DMR to Aid activity by direct targeting in vivo of the AidΔNES protein to the DNA in the zygote results in efficient and almost complete demethylation at this locus. Hence demethylation can occur in cell types in which epigenetic reprogramming occurs physiologically, suggesting that these totipotent or pluripotent cells may possess additional factors that interact with Gal4-Aid to allow it to demethylate DNA, probably by increasing its efficiency of deaminating 5-methylcytosine.

For SCNT, one of the key issues is that donor cell epigenetic marks, including DNA methylation, are reprogrammed very inefficiently when the nuclei are transferred to a recipient oocyte. This is one of the key explanations for why cloning is presently highly inefficient and cloned animals, should they survive, can exhibit a number of different abnormalities. For the early development and survival of cloned animals, it is undoubtedly important that they express pluripotency genes such as Oct4, Nanog, and SOX-2. The promoters of these genes are normally methylated in somatic cells in which the genes are inactive. It has been shown that demethylation of promoters is inefficient when the nuclei are transferred to oocytes, thus leading to insufficient expression of pluripotency genes, and as a consequence, poor development. Targeting of cytidine deaminase activity to a select number of pluripotency promoters in the donor cell genome prior to SCNT in the somatic cell can result in demethylation of these loci, and improved success in SCNT. As described previously, this targeted demethylation can be mediated via fusion of DNA binding domains from transcription factors known to bind to the promoter region of the target gene of interest. The promoter region for nanog is known to contain binding sites for Oct-4, SOX-2, Sp1 and Sp3 transcription factors. Hence, in an embodiment of the invention the DNA binding region from any one of these transcription factors can be combined with a cytidine deaminase activity, such as that mediated by Aid, in order to obtain a demethylation factor that targets the nanog promoter.

The improvement in SCNT technology described above would be of great value in order to improve prospects for stem cell therapy in human patients, where somatic cells are taken from the patient, could then be treated with cytidine deaminase, and converted into stem cells by SCNT. In addition the treatment with Aid (and possibly other reprogramming factors) could also result in reprogramming of the somatic cells directly so that they become more 'stem cell like'. This prospect would in the long run allow the production of stem cells for therapy without recourse to SCNT, and would thus avoid many ethical problems.

Another related area of application is in cancer therapy. Most if not all cancers undergo epigenetic changes, including significantly the methylation and silencing of tumour suppressor genes. Demethylation of tumour suppressor genes can ameliorate cancer phenotype. Hence, a method of targeting demethylation in vivo to tumour suppressor genes is a very promising avenue to cancer therapy. The invention has particular relevance to therapeutics directed at targeting putative cancer stem cells since they are believed to aberrantly reproduce many aspects of the normal developmental programme.

Targeting of cytidine deaminase activity to genes of interest in cancer can include, for example, fusion of the cytidine deaminase to a tumour suppressor DNA binding domain—such as the zinc finger DNA core binding region of the p53 protein. It is believed that in many cancers, mutation of the DNA binding domain of p53 can contribute to transformation. In addition, the promoter regions of many tumour suppressor genes, including p53 targets, are methylated in cancer cells.

There is also increasing overlap between the areas of stem cell biology and oncology, particularly with regard to the cancer stem cell theory and also the appreciation that p53 plays a crucial role in regulating the rate of differentiation in human ES cells (Qin et al. 2007). It is conceivable that the strategies described above for use in regulating methylation of genes involved in pluripotency could also be of interest in control of cancer development and progression. Hence, the present invention also provides to methods and compositions for the treatment of cancer.

Therapeutic embodiments of the present invention comprise pharmaceutical compositions that can be directed towards the treatment of cancer—for both solid tumours and lymphatic cancers. In the compositions of the invention a fusion polypeptide is provided comprising at least a cytidine deaminase domain and at least a DNA binding domain. The DNA binding domain may be either specific to a target DNA sequence or a non-specific polypeptide domain with DNA binding affinity. The therapeutic compositions of the invention also typically comprise a pharmaceutically acceptable carrier.

Pharmaceutical preparations of the invention are formulated to conform with regulatory standards and can be administered orally, intravenously, topically, or via other standard routes. The pharmaceutical preparations may be in the form of tablets, pills, lotions, gels, liquids, powders, suppositories, suspensions, liposomes, microparticles or other suitable formulations known in the art.

For therapeutic purposes, the pharmaceutical preparations of the present invention may be utilised as the primary form of cancer therapy. In this way it is envisaged that the demethylation activity is targeted to sites in the promoters of tumour suppressor genes that are known to be methylated in the specific cancer cell to be treated (including p53) so as to induce 'reactivation' of these tumour suppressor genes and consequent apoptosis or cell cycle arrest in the target cancer cell. Alternatively, the pharmaceutical preparations of the invention can be used as adjuncts to conventional cancer chemotherapeutics and other anti-cancer drugs. In this way, the pharmaceutical compositions of the invention can increase the susceptibility of the cancer cells to treatment with the conventional pharmaceutical approach, by reducing the inherent 'resistance' of the cancer cells to the chemotherapeutic agent.

It is evident, that the compositions of the present invention provide a unique epigenetic route to treatment of cancers.

The molecules and pharmaceutical compositions of the present invention can be assessed for their anti-cancer/anti-tumorigenic effects by utilising in vitro and ex vivo assays. In one suitable assay, a nucleic acid vector that expresses a molecule of the invention is transfected into a cancer cell line (e.g. HeLa cell line). Appropriate controls are established comprising the cancer cell line transfected with vector backbone only, or vector plus a molecule of the invention in which the cytidine deaminase domain is rendered non-functional (e.g. see the AAid2 domain) described in more detail below. Induced apoptosis in the cancer cell line transfected with the molecules of the invention but not in the control cells would be indicative of an anti-cancer effect for the molecule of the invention.

A suitable ex vivo assay assesses the ability of the molecules of the invention to inhibit tumour formation in an organism. The assay involves transfecting a cancer cell line (e.g. NIH-3T3 cells) with nucleic acid vectors, such as those described above, and then injecting the transfected cells subcutaneously into nude mice. Rapidly growing tumours would be expected in mice injected with the vector backbone only or a molecule with a non-functional cytidine deaminase domain by 21 days post injection. The animals injected with cells transfected with molecules of the invention that exhibit targeted cytidine deaminase activity and which successfully demethylate promoter regions of silenced tumour suppressor genes, would be expected to either not exhibit tumour growth, or exhibit reduced or diminished tumours. This assay could be used to screen many targeted and non-targeted variants of the molecules of the invention. For instance, the ex vivo assay is particularly suited for screening of several fusion molecules comprising the cytidine deaminase domain of Aid (e.g. AidΔNES) or Apobec1 with different DNA binding domains (e.g. zinc finger domains).

A specific embodiment of the invention provides for a transgenic animal comprising a nucleic acid sequence that expresses a molecule of the invention. Methods suitable for producing transgenic animals are described, for example in European Patent No. 419621. Optionally, the nucleic acid sequence is inducible in response to an exogenous factor. The inducible promoter sequence may be a heterologous sequence that is introduced at the same time as the nucleic acid sequence that expresses a molecule of the invention. Alternatively, the inducible promoter sequence may be an endogenous sequence that is present normally in the genome of the target cell. Transgenic animals of the invention can express molecules exhibiting either targeted or non-targeted demethylation activity and are therefore of considerable use in drug screening models or as a system for investigating systems biology associated with erasure of genetic imprints. In a specific embodiment of the invention, the transgenic animal of the invention is a mouse comprising a stably integrated gene that expresses a polypeptide including an AidΔ-NES domain and a non-specific DNA binding domain. The integrated gene comprises a heterologous promoter that is inducible in response to exposure of the animal to an exogenous factor, such as a steroid hormone or a molecule such as tamoxifen or Tet. In this way, widespread demethylation of the DNA can be controllably induced in the animal or in cells taken from the animal—i.e. in culture—and used to investigate the mechanisms involved in cancer development and progression.

In accordance with the invention, nucleic acid vectors suitable for transfection of the target cell of interest are used. The vectors are designed according to conventional protocols for the intended use, such as for expression of the molecules of the invention, and/or stable integration into the genome of the target cell (Sambrook J. et al, Molecular Cloning: a Laboratory Manual, Cold Spring Harbor Press, Cold Spring Harbor, N.Y.). In its broadest sense, the vectors of the invention encompass a DNA molecule that is either linear or circular, into which other DNA sequence fragment(s) of appropriate size can be integrated, and wherein the DNA fragment(s) include the nucleic acid sequences encoding the molecules of the invention and, optionally, additional segments that provide for transcription of the sequence encoded by the DNA sequence fragment. The additional segments can include and are not limited to: promoters, transcription terminators, enhancers, internal ribosome entry sites, untranslated regions, polyadenylation signals, selectable markers, origins of replication, homologous DNA flanking regions and such like. Suitable vectors are often derived from plasmids, cosmids, viral vectors and yeast artificial chromosomes; vectors are often recombinant molecules containing DNA sequences from several sources.

In a specific embodiment of the invention an expression vector comprises a first nucleic acid sequence that encodes a polypeptide sequence that exhibits a cytidine deaminase activity, the first sequence being linked to at least a second nucleic acid sequence that encodes a polypeptide sequence that confers a DNA binding activity. The 'linkage' between the first and second sequences can be direct in the sense that the two domains are spatially proximate. In alternative embodiments of the invention the linkage may be less direct in the sense that one or more intervening polypeptide sequences can be included to assist with tertiary conformation, cellular regulation, labelling or protein purification.

The invention is now described in more detail by way of the following non-limiting examples.

EXAMPLES

Example 1

We wished to determine if targeting of Aid protein in vivo to a highly methylated region such as an imprinted region could lead to its demethylation. We chose the paternally methylated region upstream of the H19 gene into which we introduced a Gal4 binding site (UAS) to which a transgenically expressed Gal4 fusion protein binds in vivo (Murrell et al 2004). We then made transgenic strains of mice that expressed a Gal4-Aid fusion protein from the ubiquitous CMV promoter (FIG. 1). From this fusion protein we deleted the nuclear export signal of Aid, which normally keeps Aid in the cytoplasm (Barreto et al, 2003), so as to generate the Gal4-AidΔNES construct (SEQ ID NO:2).

We bred males with the UAS binding site in the H19 DMR to females carrying the Gal4-AidΔNES expressing transgenes (SEQ ID NO:2), and analysed DNA methylation in offspring. Strikingly, the paternally inherited DMR was largely unmethylated (FIG. 2), while the maternal allele in the same mice remained unmethylated as expected. As a control for the presence of the UAS sequence and of proteins bound to the paternal allele of the H19 DMR we analysed the paternally derived DMR with the UAS bred with control transgenic mice expressing a Gal4-myc fusion protein, which locates in vivo to the DMR (Murrell et al 2004, also WO-A-04106550). This allele remained fully methylated just as the wildtype paternal one (FIG. 2).

Aid and Apobec1 and 3 can deaminate cytosine in DNA leading to hypermutation of DNA in immunoglobulin genes and viruses (Petersen-Mahrt 2005). Deamination of cytosine results in uracil which is normally efficiently repaired by the mismatch glycosylases Ung and Smug, but this repair may be rate limiting in somatic hypermutation of immunoglobulin genes (DiNoia et al 2006). Similarly, deamination of 5 methylcytosine can be mutagenic if the resulting T:G mismatches are not repaired efficiently within the same cell cycle. We therefore sequenced 42 H19 DMR-UAS paternal chromosomes from offspring with Gal4-AidΔNES transgenes (SEQ ID NO:2), in which approximately 90% of CpGs were demethylated, as shown in FIG. 2. All sequences were wildtype, and mutations were therefore not found at this level of detection (data not shown). We conclude that T:G mismatch repair is efficient and is not rate limiting for demethylation of 5 methylcytosine by the deamination mechanism.

Materials and Methods

The generation of the H19 DMR UAS and of the CMV Gal4-myc mice have been described (Murrell et al 2004 also WO-A-04106550). The CMV Gal4-AidΔNES transgene (SEQ ID NO:2) was constructed by fusing Aid in-frame with the Gal4 DNA binding domain. We amplified Aid cDNA (NM_009645) without nuclear export sequence (NES) at the C-terminus (nts 93-600) by PCR with appropriate sets of primers and cloned it into the BamHI-EcoRI sites of the pcDNA3.1-Gal4 vector (Fuks et al., 2001). The construct was verified by DNA sequencing (see FIG. 4).

The CMV Gal4-AidΔNES DNA fragment (SEQ ID NO:2) (see FIG. 1b) was then linearized by NruI and DraIII enzymes and microinjected into F1×F1 mouse zygotes. From five positive founder mice, three permanent transgenic lines were established (termed lines 4, 5, and 7). These were bred with the H19 DMR UAS mice as described in the text. DNA was isolated from neonatal organs by standard methods, was bisulphite treated as described (Oswald et al., 2000) and amplified with outer and inner primers;

```
                                       (SEQ ID NO: 4)
F1:  5'-GTAAGATGTGTGTATTTTTGGAATG-3'
and (SEQ ID NO: 5)
R1:  5'-AATCCCTAACTTCTCCTAATCTCTA-3';

(SEQ ID NO: 6)
F2:  5'-GTAAGATGTGTGTATTTTTGGAAT-3'
and (SEQ ID NO: 7)
R2:  5'-CAACCAAACTAACTTAACTACAAATC-3'
``` under the following conditions; Thirty-five cycles of 95° C. for one min followed by annealing temperature at 52° C. for one min and subsequent elongation at 72° C. for one min. PCR products were cloned into PCR2.1 using TOPO TA cloning kit (Invitrogen) according to the manufacturer's instructions. The cloned PCR fragments were then sequenced with M13 forward primers.

Our results show clearly that exposure of a fully methylated H19 DMR to Aid activity by direct targeting in vivo of the protein to the DNA results in efficient and almost complete demethylation. We do find that there are some DNA molecules (approximately 10%, FIG. 2) which remain substantially methylated, sometimes in the form of almost completely methylated individual chromosomes that are indistinguishable from the wildtype paternal ones. This may indicate that there is a rapid erasure of methylation in early embryos which is not quite complete, but that such erasure does not continue at later stages. Molecules that are substantially demethylated will bind CTCF and hence be protected from de novo methylation, while those that failed to undergo demethylation initially will remain methylated through the activity of the maintenance methyltransferase Dnmt1.

Example 2

The above example demonstrates that deletion of a specific region of the C-terminal region of Aid results in nuclear localisation of Aid but does not impair its function as a cytidine deaminase. To further verify this finding, we made two mutants of the same transgene; CMV Gal4-ΔAid1 carries two amino-acid changes, which were designed to affect its catalytic function and its DNA binding, respectively, and CMV Gal4-ΔAid2 has a single amino acid change in the catalytic domain (see FIG. 5a). Both CMV Gal4-ΔAid1 and CMV Gal4-ΔAid2 lack the C-terminal NES. Plasmids CMV Gal4-ΔAid1 and CMV Gal4-ΔAid2 were derived from CMV Gal4-AidΔNES (SEQ ID NO:2) by standard in vitro mutagenesis and were verified by sequencing.

Four independent transgenic lines were established. Two of the lines were made (as described above in Example 1) with CMV Gal4-AidΔNES (SEQ ID NO:2) (denoted as lines TG 4 and 5), the third with CMV Gal4-ΔAid1 (denoted as line TG7), and the fourth with CMV Gal4-ΔAid 2 (denoted as line TG8). In all lines the transgenes were expressed in embryos and placentas on E12.5, and in postnatal tissues notably in the ovary, with some exceptions such as the liver (FIG. 5b, see further discussion in Example 3 below). The RT PCR results were confirmed by Western blotting using an antibody against the DNA binding domain of Gal4 (data not shown). Expression was also analysed by immunofluorescence in 1 cell zygotes produced from transgenic females of lines TG5 and 7. Gal4-AidΔNES (SEQ ID NO:3) or Gal4-ΔAid1 protein was clearly detected in strains TG5 and 7, respectively, and was localised in the pronuclei of the zygotes as expected from deleting the nuclear export signal (FIG. 5c). This shows that the fusion protein is present in oocytes before fertilisation, in agreement with detecting mRNA in the ovary, and is rapidly translocated into the pronuclei as they form.

Example 3

Analysis of methylation in neonatal liver (in which the transgenes are not expressed, see FIG. 5b) was undertaken and the same extent of demethylation (approximately 90%) was found (while the maternal allele in the same mice remained unmethylated as expected). This shows that transgene expression in somatic tissues is not necessary for maintenance of the hypomethylated state. Maintenance of hypomethylation may occur because insulator proteins such as CTCF can bind to the demethylated allele and thus protect it from de novo methylation (Schoenherr et al., 2003). Demethylation was consistently observed in all transgenic offspring of the CMV Gal4-AidΔNES (SEQ ID NO:2) transgenic lines 4 and 5, however, no demethylation was observed in strains 7 and 8 which express the mutant forms of Aid (FIG. 6). As an additional control for the presence of the UAS sequence and for ectopic protein binding to the paternal allele of the H19 DMR we analysed the paternally derived DMR with the UAS bred to control transgenic mice expressing CMV Gal4-myc (TG1) in which the fusion protein also locates in vivo to the DMR. This allele also remained fully methylated just as the wildtype one (FIG. 6).

Since demethylation was so uniform across different tissues and developmental stages, the present results suggest that it is the presence in the zygote of the Gal4-AidΔNES protein (SEQ ID NO:3) that critical for demethylation. Hence, the results suggest that Aid mediated demethylation of the genome at an early stage in development or in precursor toti/pluripotent cells can result in sustained demethylation in cells subsequently derived from these precursors. This finding has profound implications, for example in cancer stem cells, where many tumour suppressor genes are silenced by methylation of the DNA. According to the present invention targeted demethylation in a precursor pluripotent cancer stem cell could, thus, result in sustained demethylation in downstream cancer cell derivatives and the thereby the maintenance of tumour suppressor gene expression in these downstream cancer cells.

Materials and Methods

RNA and Protein Expression of Transgenes and RNA Expression of Igf2 and H19

Total RNA was extracted from different embryonic and postnatal tissues with the RNeasy mini/midi® kit (Qiagen). cDNA was synthesized by using SuperScript™ II reverse transcriptase (Invitrogen). The efficiency of cDNA synthesis was evaluated by PCR for Hprt. To ensure there is no DNA contamination, reactions without reverse transcriptase were always done in parallel. Expression of Gal4-AidΔNES (SEQ ID NO:2) transcripts was analyzed by RT-PCR using primers in the Gal4 region (s: AAGTGCGCCAAGTGTCTGAA) (SEQ ID NO:8) and Aid region (as: CAGCCAGACTTGTTGCGAAG) (SEQ ID NO:9) to prevent amplification of endogenous Aid transcripts. Gal4-AidΔNES protein (SEQ ID NO:3) expression was confirmed by western blotting of total protein extracted from different tissues of transgenic mice. Briefly, tissue extracts were prepared using standard protocols and the protein concentration was determined by Bradford assay. Protein samples were run on 10% SDS-polyacrylamide gels, electroblotted onto Hybond-P membranes (Amersham), blocked and incubated with 1:200 dilution of the anti-Gal4 primary antibody (Santa Cruz) and 1:2000 anti-tubulin antibody (Abcam®). The membrane was then incubated with 1:2000/1:10000 dilution of secondary antibody (Amersham) against rabbit/goat immunoglobulin. Detection was done with the enhanced chemiluminescence system (ECL, Amersham). Expression levels of Igf2 (Mm00439565_g1), H19 (Mm01156721_g1), and Gapdh (Mm99999915_g1) transcripts were determined by Taq-Man® probes purchased from Applied Biosystems. Quantitative real time PCR experiments were performed in triplicate with a ABI PRISM 7700 thermocycler (Applied Biosystems); the relative quantification, amplification efficiencies, and comparative method of relative quantification were done according to instructions supplied by Qiagen.

Gal4 Staining of Fertilised Oocytes

Fertilised oocytes were washed in PBS, and after fixation in 4% paraformaldehyde in PBS for 15 minutes, the zonae were removed with Tyrode's Solution Acidic (Sigma) and the oocytes permeabilised with 0.2% Triton X-100 in PBS for 1 hour, at room temperature. After blocking in 0.05% Tween-20 in PBS containing 1% BSA (BS) overnight at 4° C., the oocytes were incubated with anti-Gal4 rabbit polyclonal antibody (Santa Cruz, sc-577) diluted 1:30 (BS) for 3 hours at room temperature. Detection was achieved using goat α-rabbit IgG-Alexa (Molecular Probes) as secondary antibody. DNA was stained with DAPI (5 µg/ml) and all samples were mounted in Slow Fade (Molecular Probes). Image acquisition was performed with a LSM 510 Meta confocal laser scanning microscope (Carl Zeiss) equipped with a "Plan-Apochromat" 63×/1.40 DIC oil-immersion objective. Final pictures were obtained by Z-stack projection of serial sections (800×800, pixel size; z-step, 0.46 µm).

Example 4

We determined the extent to which demethylation had occurred on either side of the H19 UAS targeting sequence. On the 3' side of the UAS sequence efficient demethylation of the paternal allele was also observed which extended to at least 600 bp downstream including the G-repeat region. On the 5' side, there was a sharp drop of demethylation around the 3rd CTCF binding site, but there was evidence for demethylated CpGs further upstream. Hence, the demethylation activity of the Gal4-AidΔNES protein (SEQ ID NO: 3) is exerted over a large region despite being associated with the GAL4 site specific DNA binding domain. It is envisaged that the choice of the DNA binding domain might also contribute to the control of the extent of AidΔNES activity.

Although particular embodiments of the invention have been disclosed herein in detail, this has been done by way of example and for the purposes of illustration only. The aforementioned embodiments are not intended to be limiting with respect to the scope of the appended claims, which follow. It is contemplated by the inventors that various substitutions, alterations, and modifications may be made to the invention without departing from the spirit and scope of the invention as defined by the claims.

REFERENCES

Altschul et al., 1997, *Nucleic Acids Res.*, 25, pp 3389-3402

Barreto V, Reina-San-Martin B, Ramiro A R, McBride KM, Nussenzweig MC. C-terminal deletion of AID uncouples class switch recombination from somatic hypermutation and gene conversion Mol. Cell. 2003 August; 12(2):501-8.

Baylin S B. DNA methylation and gene silencing in cancer. Nat Clin Pract Oncol. 2005 December; 2 Suppl 1:S4-11. and Lyko F, Brown R. DNA methyltransferase inhibitors and the development of epigenetic cancer therapies J Natl Cancer Inst. 2005 Oct. 19; 97(20):1498-506.

Di Noia, J. M., Rada, C., and Neuberger, M. S. (2006) SMUG1 is able to excise uracil from immunoglobulin genes: insight into mutation versus repair EMBO J 25, 585-595.

Egger G, Liang G, Aparicio A, Jones P A. Epigenetics in human disease and prospects for epigenetic therapy Nature May 2004; 429: 457-63.

Feinberg A P & Vogelstein B; Hypomethylation distinguishes genes of some human cancers from their normal counterparts Nature. 01(5895):89-92, January 1983.

Fuks, F., Burgers, W. A., Godin, N., Kasai, M., and Kouzarides, T. (2001). Dnmt3a binds deacetylases and is recruited by a sequence-specific repressor to silence transcription EMBO J. 20, 2536-2544.

Henikoff & Henikoff, 1992, Proc. Natl. Acad. Sci. USA, 89, pp 10915

Klein G. Epigenetics: surveillance team against cancer Nature 2005 Mar. 10; 434(7030):150.

Morgan, H. D., Dean, W., Coker, H. A., Reik, W., and Petersen-Mahrt, S. K. (2004) Activation-induced cytidine deaminase deaminates 5-methylcytosine in DNA and is expressed in pluripotent tissues: implications for epigenetic reprogramming J Biol Chem 279, 52353-52360.

Murrell, A., Heeson, S., and Reik, W. (2004) Interaction between differentially methylated regions partitions the imprinted genes Igf2 and H19 into parent-specific chromatin loops Nat Genet. 36, 889-893.

Muto T., Muramatsu M., Taniwaki M. Kinoshita K and Honjo T Isolation, tissue distribution, and chromosomal localization of the human activation-induced cytidine deaminase (AID) gene Genomics. 2000 Aug. 15; 68(1):85-8 Neuberger et al. Trends Biochem. Sci. (2003) 28:308-312

Oswald, J., Engemann, S., Lane, N., Mayer, W., Olek, A., Fundele, R., Dean, W., Reik, W., and Walter, J. (2000) Active demethylation of the paternal genome in the mouse zygote Curr Biol 10, 475-478.

Petersen-Mahrt, S. (2005) DNA deamination in immunity Immunol Rev 203, 80-97.

Qin H. et al. (2007) Regulation of Apoptosis and Differentiation by p53 in Human Embryonic Stem Cells J. Biol. Chem. 28(8): 5842-5852

Rada, C et al. Proc Natl Acad Sci USA. 2002 May 14; 99(10): 7003-8

Schoenherr C J, Levorse J M and Tilghman S. M. CTCF maintains differential methylation at the Igf2/H19 locus Nat. Genet. 2003; 33:66-69

Ushijima T. Epigenetic field for Cancerization J. Bio. Mol. Biol. 2007; 40(2):142-150

Wilmut I, Beaujean N, de Sousa P A, Dinnyes A, King T J, Paterson L A, Wells D N, Young LE. Somatic cell nuclear transfer. Nature. 2002 Oct. 10; 419(6907):583-6. Yoo C B & Jones P A. Epigenetic therapy for cancer; part, present and future. Nature Review Drug Discovery January 2006; 37-50.

The invention claimed is:

1. An isolated polypeptide molecule capable of initiating a demethylation of a methylated DNA sequence in a eukaryotic cell, the molecule consisting of a first domain that exhibits a cytidine deaminase activity, wherein the first domain consists of the AidΔNES sequence encoded by SEQ ID NO:1, and a second domain that confers a DNA binding activity.

2. The molecule of claim 1, wherein the second domain comprises a non-sequence specific DNA binding domain.

3. The molecule of claim 1, wherein the second domain comprises a sequence specific DNA binding domain.

4. The molecule of claim 3, wherein the sequence specific DNA binding domain comprises a domain selected from the group consisting of: a zinc finger domain; a leucine zipper domain; a helix-turn-helix domain; a steroid receptor DNA binding domain; and a homeodomain.

5. The molecule of claim 3, wherein the sequence specific DNA binding domain is targeted to bind a sequence present in the promoter region of a gene.

6. The molecule of claim 1, wherein the cell is a mammalian cell.

7. The molecule of claim 1, wherein the cell is a human cell.

8. The molecule of claim 1, wherein the cell is a pluripotent cell.

9. The molecule of claim 1, wherein the cell is a somatic cell.

10. The molecule of claim 1, wherein the cell is a cancer cell.

11. A pharmaceutical composition comprising the molecule of claim 1 and a pharmaceutically acceptable carrier.

* * * * *